(12) United States Patent
Selby et al.

(10) Patent No.: US 11,452,808 B2
(45) Date of Patent: Sep. 27, 2022

(54) FLUID FLOW SENSING

(71) Applicant: ConvaTec Technologies Inc., Las Vegas, NV (US)

(72) Inventors: Robert Gordon Maurice Selby, Royston (GB); Arnau Perdigo-Oliveras, Royston (GB); Roderick Marcus Van Den Bergh, Royston (GB)

(*) Notice: Subject to any disclaimer, the term of this patent is extended or adjusted under 35 U.S.C. 154(b) by 934 days.

(21) Appl. No.: 16/316,016

(22) PCT Filed: Jul. 7, 2017

(86) PCT No.: PCT/US2017/041216
§ 371 (c)(1),
(2) Date: Jan. 7, 2019

(87) PCT Pub. No.: WO2018/009879
PCT Pub. Date: Jan. 11, 2018

(65) Prior Publication Data
US 2019/0151515 A1    May 23, 2019

Related U.S. Application Data

(60) Provisional application No. 62/360,248, filed on Jul. 8, 2016.

(51) Int. Cl.
*A61M 1/00* (2006.01)
*A61M 27/00* (2006.01)

(52) U.S. Cl.
CPC .............. *A61M 1/734* (2021.05); *A61M 1/73* (2021.05); *A61M 1/90* (2021.05); *A61M 1/98* (2021.05); *A61M 27/00* (2013.01); *A61M 2205/3306* (2013.01); *A61M 2205/3317* (2013.01); *A61M 2205/3334* (2013.01); *A61M 2205/3344* (2013.01)

(58) Field of Classification Search
CPC .......... A61M 1/60; A61M 1/982; A61M 1/98; A61M 1/0001; A61M 1/0023; A61M 1/90; A61M 2205/3344; A61M 2205/3334; A61M 2205/3306
See application file for complete search history.

(56) References Cited

U.S. PATENT DOCUMENTS

| | | | |
|---|---|---|---|
| 4,441,215 A | 4/1984 | Kaster | |
| 5,358,492 A | 10/1994 | Feibus | |
| 6,695,823 B1 | 2/2004 | Lina et al. | |
| 8,083,712 B2 | 12/2011 | Biggie et al. | |

(Continued)

FOREIGN PATENT DOCUMENTS

| | | |
|---|---|---|
| CN | 101176688 A | 5/2008 |
| CN | 103619366 A | 3/2014 |

(Continued)

OTHER PUBLICATIONS

Colombian Application No. NC2018/0005230 Office Action dated May 31, 2018.

(Continued)

*Primary Examiner* — Ariana Zimbouski
(74) *Attorney, Agent, or Firm* — Taft Stettinius & Hollister LLP; Ryan O. White; Derek B. Lavender

(57) ABSTRACT

Devices and methods for collecting and sensing fluid flow are provided.

26 Claims, 8 Drawing Sheets

(56) References Cited

U.S. PATENT DOCUMENTS

| | | |
|---|---|---|
| 8,308,714 B2 | 11/2012 | Weston et al. |
| 8,439,894 B1 | 5/2013 | Miller |
| 8,521,979 B2 | 8/2013 | Laberge et al. |
| 8,814,840 B2 | 8/2014 | Evans et al. |
| 8,858,516 B2 | 10/2014 | Hu et al. |
| 9,205,183 B2 | 12/2015 | Hartwell et al. |
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,207,031 B2 * | 2/2019 | Toth ............... A61B 5/445 |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |

(56) References Cited

U.S. PATENT DOCUMENTS

| | | |
|---|---|---|
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2006/0015019 A1 | 1/2006 | Watt et al. |
| 2006/0155260 A1 | 7/2006 | Blot et al. |
| 2006/0172000 A1 | 8/2006 | Cullen et al. |
| 2006/0173253 A1* | 8/2006 | Ganapathy ......... A61B 5/14542 607/88 |
| 2007/0185426 A1 | 8/2007 | Ambrosio et al. |
| 2007/0208300 A1 | 9/2007 | Pravong et al. |
| 2007/0219512 A1 | 9/2007 | Heaton et al. |
| 2007/0239078 A1 | 10/2007 | Jaeb |
| 2008/0082059 A1* | 4/2008 | Fink ................. A61M 1/90 604/305 |
| 2009/0082731 A1 | 3/2009 | Moreno |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0036333 A1 | 2/2010 | Schenk, III et al. |
| 2010/0069863 A1 | 3/2010 | Olson |
| 2010/0125233 A1 | 5/2010 | Edward et al. |
| 2010/0125258 A1 | 5/2010 | Coulthard et al. |
| 2010/0137775 A1 | 6/2010 | Hu et al. |
| 2010/0168719 A1* | 7/2010 | Chen ................. A61M 27/00 604/378 |
| 2010/0185163 A1 | 7/2010 | Heagle |
| 2010/0298790 A1 | 11/2010 | Guidi et al. |
| 2010/0318043 A1 | 12/2010 | Malhi et al. |
| 2010/0324516 A1 | 12/2010 | Braga et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0152799 A1 | 6/2011 | Kevin et al. |
| 2011/0172616 A1 | 7/2011 | Hartwell et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0276016 A1 | 11/2011 | Tsai |
| 2012/0016322 A1 | 1/2012 | Coulthard et al. |
| 2012/0065602 A1 | 3/2012 | Adams et al. |
| 2012/0071845 A1 | 3/2012 | Hu et al. |
| 2012/0100538 A1 | 4/2012 | Mikolajczyk et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2013/0267918 A1 | 10/2013 | Pan et al. |
| 2013/0296816 A1 | 11/2013 | Greener |
| 2014/0005618 A1 | 1/2014 | Locke et al. |
| 2014/0031771 A1 | 1/2014 | Locke et al. |
| 2014/0074053 A1 | 3/2014 | Locke et al. |
| 2014/0107599 A1 | 4/2014 | Fink et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276489 A1 | 9/2014 | Robinson et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2014/0336602 A1 | 11/2014 | Karpowicz et al. |
| 2014/0343519 A1 | 11/2014 | Weston |
| 2015/0018433 A1 | 1/2015 | Leipzig et al. |
| 2015/0057624 A1 | 2/2015 | Simmons et al. |
| 2015/0057625 A1 | 2/2015 | Coulthard |
| 2015/0071985 A1 | 3/2015 | Walker et al. |
| 2015/0073359 A1 | 3/2015 | Hudspeth et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0182677 A1 | 7/2015 | Collinson et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0290364 A1 | 10/2015 | Wall et al. |
| 2015/0320901 A1 | 11/2015 | Chandrashekhar-Bhat et al. |
| 2015/0351970 A1 | 12/2015 | Dagger et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0151547 A1 | 6/2016 | Hartwell et al. |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |

(56) References Cited

U.S. PATENT DOCUMENTS

| | | |
|---|---|---|
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |

(56) References Cited

U.S. PATENT DOCUMENTS

| | | |
|---|---|---|
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 1905465 A1 | 4/2008 |
| EP | 2711034 A1 | 3/2014 |
| EP | 2817038 A1 | 12/2014 |
| EP | 3187204 A1 | 7/2017 |
| EP | 3643328 A1 | 4/2020 |
| EP | 3643330 A1 | 4/2020 |
| EP | 3643331 A1 | 4/2020 |
| EP | 3669838 A1 | 6/2020 |

(56) References Cited

FOREIGN PATENT DOCUMENTS

| | | |
|---|---|---|
| EP | 3669843 A1 | 6/2020 |
| EP | 3669844 A1 | 6/2020 |
| GB | 2579211 A | 6/2020 |
| GB | 2579368 A | 6/2020 |
| JP | 200880137 A | 4/2008 |
| JP | 201577464 A | 4/2015 |
| WO | 2005018543 A2 | 3/2005 |
| WO | WO-2009106895 A1 | 9/2009 |
| WO | 2010068502 A1 | 6/2010 |
| WO | 2011121394 A1 | 10/2011 |
| WO | 2011135284 A1 | 11/2011 |
| WO | 2011144888 A1 | 11/2011 |
| WO | WO-2012057881 A1 | 5/2012 |
| WO | 2012142473 A1 | 10/2012 |
| WO | 2013015827 A2 | 1/2013 |
| WO | 2013039623 A1 | 3/2013 |
| WO | 2013126049 A1 | 8/2013 |
| WO | 2014014842 A1 | 1/2014 |
| WO | WO-2015052219 A1 | 4/2015 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | WO-2017068364 A1 | 4/2017 |
| WO | 2017125250 A1 | 7/2017 |
| WO | WO-2017196888 A1 | 11/2017 |
| WO | WO-2018009873 A1 | 1/2018 |
| WO | WO-2018009879 A1 | 1/2018 |
| WO | WO-2018009880 A1 | 1/2018 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |

OTHER PUBLICATIONS

Great Britain Application No. GB1608099.6 search report dated Oct. 11, 2016.
PCT/US2017/041221 International Search Report and Written Opinion dated Sep. 13, 2017.
PCT/GB2016/053295 International Preliminary Report on Patentability dated Apr. 24, 2018.
PCT/GB2016/053295 International Search Report and Written Opinion dated Jan. 17, 2017.
PCT/US2017/031817 International Search Report and Written Opinion dated Aug. 11, 2017.
PCT/US2017/031817 International Preliminary Report on Patentability dated Nov. 13, 2018.
PCT/US2017/041208 International Search Report and Written Opinion dated Sep. 8, 2017.
PCT/US2017/041216 International Search Report and Written Opinion dated Sep. 13, 2017.
PCT/US2017/041208 International Preliminary Report on Patentability dated Jan. 8, 2019.
PCT/US2017/041216 International Preliminary Report on Patentability dated Jan. 8, 2019.
PCT/US2017/041221 International Preliminary Report on Patentability dated Jan. 8, 2019.

* cited by examiner

FLUID FLOW SENSING

CROSS-REFERENCE

This application is a U.S. National Phase of International Application No. PCT/US2017/041216, filed on Jul. 7, 2017, which claims the benefit of U.S. Provisional Application No. 62/360,248, filed Jul. 8, 2016, both of which are incorporated herein by reference in their entirety.

BACKGROUND OF THE INVENTION

Wounds may be treated by providing negative pressure to the space above the wound to promote healing in a process often referred to a negative pressure wound therapy (NPWT). In monitoring the progress of the wound, it is often beneficial to monitor the rate of exudate discharged from the wound to assist in an assessment of wound healing.

SUMMARY OF THE INVENTION

Medical procedures often involve the removal of fluid and wound exudate from a patient including, for example, during negative pressure wound therapy (NPWT). For NPWT, as a negative pressure is applied over a wound site of the patient, fluid and wound exudate is drawn from the wound and collected, for example, in a dressing positioned over the wound site and/or in a canister. For systems that employ collection canisters, the volume of fluid collected is often sensed and recorded to build a picture of the rate of fluid discharge from the wound. However, this approach can be problematic due to the uncertainty of canister orientation, especially during use in portable therapies. Measurement of readings when the canister is not oriented properly can lead to false readings and assessment of the wound. It is therefore beneficial to measure the flow rate of fluid prior to or as it is drawn into the canister. Nevertheless, due to the nature of NPWT there are challenges with measuring fluid at this point because the fluid to be measured is typically a mixture of air and liquid. For example, air may be introduced into the system through small leak paths at the wound site. Therefore, there is a need for managing the flow of fluid through a system so that parameters of the fluid can be sensed. By providing an air bypass device, or fluid collection device, small quantities of liquid accumulate in the fluid collection device while air passes through the device. Once there is a significant volume of liquid collected, the liquid is released through a detection conduit as a column of liquid, or a slug, which is then measurable using a sensor.

In one aspect of the disclosure, provided are fluid collection devices comprising: (a) a housing comprising an inlet and an outlet, the inlet located at a proximal end of the housing and the outlet located at a distal end of the housing; (b) a reservoir positioned within the housing at the proximal end of the housing; (c) a plurality of channel dividers positioned within the housing between the reservoir and the distal end of the housing, the plurality of channel dividers having a proximal end and a distal end; wherein the plurality of channel dividers define a plurality of fluid channels within the housing; and (d) a liquid collection region positioned within the housing between the distal end of the plurality of channel dividers and the distal end of the housing; wherein the housing comprises one or more fluid passageways connecting the inlet and the outlet through the interior of the housing; and wherein the reservoir, the plurality of channels, and the liquid collection region are in fluid communication within the one or more fluid passageways in the housing. In some embodiments, the fluid collection device is tapered and a proximal end of the reservoir has a width greater than the width of a distal end of the liquid collection region. In some cases, the width of the proximal end of the reservoir is at least equal to, or 2 to 5 times the width of the distal end of the liquid collection region. In some embodiments, the liquid collection region is configured to receive a slug of liquid having a volume between about 10 uL and about 200 uL. In some embodiments, the interior of the housing is configured to hold between about 100 uL and about 1000 uL of fluid. In some embodiments, the width of the liquid collection region is smaller near the distal end of the housing than the width of the liquid collection region near the proximal end of the housing. In some embodiments, the width of the liquid collection region is between about 0.5 mm and about 8 mm. In some embodiments, the length of the reservoir is between about 5 mm and about 50 mm. In some embodiments, the length of one or more of the plurality of channel dividers is between about 2 mm and about 50 mm. In some embodiments, the height of the reservoir is between about 0.1 mm and about 5 mm. In some embodiments, the height of one or more of the plurality of channel dividers is between about 0.1 mm and about 5 mm. In some embodiments, the width of one or more of the plurality of channels is between about 0.1 mm and about 5 mm. In some embodiments, the width of one or more of the plurality of channels is tapered to reduce direction of flow by about 1 degree to about 20 degrees. In some embodiments, the plurality of channels is from about 2 to about 15 channels. In some embodiments, the housing comprises a planer surface from the proximal end to the distal end of the housing. In some embodiments, the housing comprises a curved surface from the proximal end to the distal end of the housing.

In some embodiments, a surface of the reservoir, plurality of channels, liquid collection region, or a combination thereof comprises a hydrophobic material. In some cases, the hydrophobic material is coated on the surface by plasma treatment. In some cases, the hydrophobic material has a water contact angle greater than or equal to about 155°. In some embodiments, a surface of the reservoir, plurality of channels, liquid collection region, or a combination thereof comprises polytetrafluoroethylene (PTFE). In some embodiments, the housing comprises a plastic material. In some embodiments, the housing comprises a transparent material.

Further provided are canisters comprising any fluid collection device described herein. Further provided are canisters operably connected to any fluid collection device described herein. In another aspect of the disclosure, provided are systems comprising any fluid collection device described herein. In some embodiments, provided are fluid collection systems comprising any fluid collection device described herein and a canister, wherein the outlet of the fluid collection device is in fluid communication with an inlet of the canister. In some embodiments, provided are fluid collection systems comprising any fluid collection device described herein and a wound dressing, wherein the inlet of the fluid collection device is in fluid communication with an outlet of the wound dressing.

In some embodiments, provided are fluid collection systems comprising any fluid collection device described herein and a sensing device comprising: (a) source of negative pressure; and (b) a plurality of sensors situated within a casing such that a column of liquid located outside of the casing is in the field of view of the plurality of infrared sensors. In some cases, one or more of the plurality of sensors is an infrared sensor. In some embodiments, the casing comprises a thin layer of plastic within the field of view of the plurality of infrared sensors. In some cases, the thin layer has a thickness up to about 5 mm. In some cases, the plastic comprises polyvinyl chloride, polycarbonate, polystyrene, polyester film, or a combination thereof. In some embodiments, the casing comprises one or more windows within the field of view of the plurality of infrared sensors. In some cases, the one or more windows are transmissive to infrared at a wavenumber between about 3000 cm$^{-1}$ to about 4000 cm$^{-1}$. In some cases, the one or more windows have a thickness between about 0.1 mm and about 5 mm. In some cases, the one or more windows comprise polyvinyl chloride, polycarbonate, high density polyethylene, polystyrene, or a combination thereof. In some embodiments, the fluid collection system further comprises a light source situated within the interior of the casing such that the column of liquid located outside of the casing is in the path of the light source. In some embodiments, the plurality of infrared sensors is two or more reflective optical sensors. In some embodiments, the source of negative pressure comprises a diaphragm pump. In some embodiments, a first infrared sensor in the plurality of infrared sensors is positioned between about 0.5 cm and about 10 cm from a second infrared sensor in the plurality of infrared sensors. In some embodiments, the fluid collection system further comprises one or more pressure sensors. In some cases, one of the one or more pressure sensors is configured to detect a pressure of a wound environment by measuring a pressure at a first end of a conduit positioned within the casing, wherein the second end of the conduit is positioned at the wound environment. In some cases, one of the one or more pressure sensors is configured to detect a pressure of a canister by measuring a pressure at a first end of a conduit positioned within the casing, wherein the second end of the conduit is positioned within the canister; and wherein the conduit is configured to apply a negative pressure from the source of negative pressure to the canister. In some cases, the fluid collection system further comprises a controller configured to control an amount of negative pressure applied by the source of negative pressure. In some cases, the controller controls the amount of negative pressure applied by the source of negative pressure in response to a measurement of pressure by the one or more pressure sensors. In some embodiments, the fluid collection system further comprises a display for displaying one or more parameters of the column of liquid corresponding to measurements of the column of liquid taken by the plurality of infrared sensors. In some embodiments, the fluid collection system further comprises a power source. In some embodiments, the sensing device does not comprise a power source and power is supplied to the sensing device by an external unit connected to the sensing device. Further provided are fluid sensing systems comprising any fluid collection system described herein and a canister.

In another aspect of the disclosure, provided are fluid flow sensing systems comprising: (a) a fluid collection device comprising a housing having an inlet located at a proximal end of the fluid collection device and an outlet located at a distal end of the fluid collection device, the interior of the housing comprising: a reservoir, a plurality of channel dividers defining a plurality of fluid channels, and a liquid collection region; wherein the housing comprises one or more fluid passageways connecting the inlet and the outlet through the interior of the housing; and wherein the reservoir, the plurality of channels, and the liquid collection region are in fluid communication within the one or more fluid passageways in the housing; (b) a canister comprising an inlet and an outlet, the inlet of the canister configured to be in fluid communication with the outlet of the fluid collection device housing via a detection conduit; and (c) a sensing device comprising: a casing having an inlet, a source of negative pressure and a plurality of sensors; the inlet of the sensing device casing configured to be in fluid communication with the outlet of the canister via a negative pressure conduit. In some embodiments, the inlet of fluid collection device is configured to be connected to a wound site of a patient via a wound conduit. In some embodiments, the detection conduit has an inner diameter of less than or equal to about 0.5 mm to about 5 mm. In some embodiments, the fluid collection device and canister are configured to withstand a negative pressure applied by the source of negative pressure between about 80 and about 125 mmHg below atmospheric pressure. In some embodiments, the fluid collection device is integral with the canister. In some embodiments, the source of negative pressure comprises a diaphragm pump. In some embodiments, at least a portion of the negative pressure conduit is housed within a connector. In some cases, the connector comprises a power source. In some embodiments, the detection conduit comprises a material transmissive of infrared at a wavenumber between about 3000 cm$^{-1}$ to about 4000 cm$^{-1}$. In some embodiments, the detection conduit has a thickness between about 0.1 mm and about 5 mm. In some embodiments, the detection conduit comprises polyvinyl chloride, polycarbonate, high density polyethylene, polystyrene, or a combination thereof. In some embodiments, the plurality of fluid channels are configured to accumulate between about 10 uL and about 200 uL of liquid. In some embodiments, the sensing device further comprises a pressure sensor configured to detect a pressure within the negative pressure conduit. In some embodiments, the fluid collection device is tapered and a proximal end of the fluid collection device has a width greater than the width of a distal end of the fluid collection device. In some cases, the width of the proximal end of the fluid collection device is at least about 2 to 5 times the width of the distal end of the fluid collection device. In some embodiments, a first width of the liquid collection region is between about 1 mm and about 8 mm. In some cases, the liquid collection region is tapered and a second width of the collection region is between about 0.5 and about 7 mm. In some embodiments, the length of one or more of the plurality of channel dividers is between about 2 mm and about 50 mm. In some embodiments, the height of the interior of the housing is between about 0.1 mm and about 5 mm. In some embodiments, the width of one or more of the plurality of channels is between about 0.1 mm and about 5 mm. In some embodiments, the plurality of channels is from about 2 to about 15 channels. In some embodiments, the housing comprises a planer surface between the proximal end and distal end of the of the fluid collection device. In some embodiments, the housing comprises a curved surface between the proximal end and distal end of the of the fluid collection device.

In some embodiments, a surface of the reservoir, plurality of channels, collection region, or a combination thereof comprises a hydrophobic material. In some cases, the hydrophobic material is coated on the surface by plasma treatment. In some cases, the hydrophobic material has a water contact angle greater than or equal to about 155°. In some embodiments, a surface of the reservoir, plurality of channels, liquid collection region, or a combination thereof comprises polytetrafluoroethylene (PTFE). In some embodiments, the housing comprises a plastic material. In some embodiments, the housing comprises a transparent material.

In some embodiments, the casing comprises a thin layer of plastic material within the field of view of the plurality of sensors. In some cases, the thin layer has a thickness up to about 5 mm. In some cases, the plastic material comprises polyvinyl chloride, polycarbonate, polystyrene, polyester film, or a combination thereof. In some embodiments, the casing comprises one or more windows within the field of view of the plurality of infrared sensors. In some cases, the one or more windows are transmissive to infrared at a wavenumber between about 3000 cm$^{-1}$ to about 4000 cm$^{-1}$. In some cases, the one or more windows have a thickness between about 0.1 mm and about 5 mm. In some embodiments, the one or more windows comprise polyvinyl chloride, polycarbonate, high density polyethylene, polystyrene, or a combination thereof.

In some embodiments, the sensing device further comprises a light source. In some embodiments, the plurality of sensors is two sensors. In some embodiments, one or more of the plurality of sensors is an infrared sensor. In some embodiments, a sensor in the plurality of sensors is positioned between about 0.5 cm and about 10 cm from a second sensor in the plurality of sensors. In some embodiments, the sensing device further comprises a controller configured to control the amount of negative pressure applied by the source of negative pressure. In some embodiments, the sensing device further comprises a display for displaying one or more parameters of a column of liquid corresponding to measurements of the column of liquid taken by the plurality of sensors as the column of liquid passes through the detection conduit. The sensing device further comprising a power source. In some embodiments, the sensing device does not comprise a power source and power is supplied to the sensing device by an external unit connected to the sensing device.

In another aspect of the disclosure, provided are methods for sensing fluid flow, the methods comprising: (a) providing: (i) a fluid collection device comprising a housing having an inlet located at a proximal end of the fluid collection device and an outlet located at a distal end of the fluid collection device, the interior of the housing comprising: a reservoir, a plurality of channel dividers defining a plurality of fluid channels, and a liquid collection region; wherein the housing comprises one or more fluid passageways connecting the inlet and the outlet through the interior of the housing; and wherein the reservoir, the plurality of channels, and the liquid collection region are in fluid communication within the one or more fluid passageways in the housing; (ii) a canister comprising an inlet and an outlet, the inlet of the canister in fluid communication with the outlet of the fluid collection device housing via a detection conduit; and (iii) a sensing device comprising: a casing having an inlet, a source of negative pressure and a plurality of sensors; the inlet of the sensing device casing in fluid communication with the outlet of the canister via a negative pressure conduit; (b) applying a negative pressure from the source of negative pressure to the fluid collection device via the canister to draw a fluid mixture of liquid and air through the inlet of the fluid collection device and along the one or more fluid passageways of the fluid collection device housing; wherein the liquid of the fluid mixture accumulates at the plurality of flow channels while the air of the fluid mixture passes through flow channels until the plurality of flow channels have accumulated liquid of the fluid mixture; (c) drawing the accumulated fluid into the liquid collection region as a slug of liquid when the plurality of flow channels become blocked with the accumulated fluid; (d) drawing the slug from the liquid collection region, through the outlet of the fluid collection housing, and through the detection conduit; and (e) detecting passage of the slug through the detection conduit with the plurality of sensors. In some embodiments, the time it takes for the beginning of the slug to reach each of the plurality of sensors is detected successively; and wherein the time it takes for the end of the slug to reach each of the plurality of sensors is detected successively. In some embodiments, the method further comprises comparing the time delay between the beginning and the end of the liquid slug passing the plurality of sensors to calculate the speed and length of the slug. In some embodiments, the method further comprises calculating the rate of the flow of the mixture from the fluid collection device.

In some embodiments, the inlet of fluid collection device is connected to a wound site of a patient via a wound conduit, and the fluid mixture drawn through the inlet of the fluid collection device is fluid drawn from the wound site of the patient. In some cases, the fluid collection device is connected to the wound site of the patient in an orientation-independent manner. In some embodiments, the detection conduit has an inner diameter of about 0.5 mm to about 5 mm. In some embodiments, the negative pressure applied is between about 80 and about 125 mmHg below atmospheric pressure. In some embodiments, the volume of the slug is between about 10 and about 200 uL. In some embodiments, the length of the slug is between about 3 mm and about 100 mm. In some embodiments, the fluid mixture comprises less than about 5% of air by volume. In some embodiments, the fluid mixture comprises greater than about 5% of air by volume. In some embodiments, the fluid mixture provided to the fluid collection device comprises less than about 1% of liquid by volume. In some embodiments, the fluid mixture provided to the fluid collection device comprises greater than about 1% of liquid by volume. In some cases, the fluid mixture is exudate from a wound site of a patient sealed with a dressing, and the liquid and air composition of the fluid mixture is dependent on: the rate of exudate flow from the patient, the rate of air leak into the dressing, or a combination thereof. In some embodiments, the fluid collection device is integral with the canister. In some embodiments, the source of negative pressure comprises a diaphragm pump. In some embodiments, at least a portion of the negative pressure conduit is housed within a connector. In some cases, the connector comprises a power source.

In some embodiments, the detection conduit comprises a material transmissive to infrared at a wavenumber between about 3000 cm$^{-1}$ to about 4000 cm$^{-1}$. In some embodiments, the detection conduit comprises a material having a thickness between about 0.1 mm and about 5 mm. In some embodiments, the detection conduit comprises polyvinyl chloride, polycarbonate, high density polyethylene, polystyrene, or a combination thereof. In some embodiments, the plurality of fluid channels are configured to accumulate between about 10 uL and about 200 uL of liquid. In some embodiments, the method further comprises sensing a pressure within the negative pressure conduit with a pressure sensor positioned within the casing of the sensing device. In some cases, the application of negative pressure from the source of negative pressure is modulated to maintain a predetermined pressure within the negative pressure conduit. In some embodiments, the fluid collection device is tapered and a proximal end of the fluid collection device has a width greater than the width of the distal end of the fluid collection device. In some cases, the width of the proximal end of the fluid collection device is at least about 5× the width of the distal end of the fluid collection device. In some embodiments, a first width of the liquid collection region is between about 1 mm and about 8 mm. In some cases, a second width of the liquid collection region is between about 0.5 and about 7 mm. In some embodiments, the length of one or more of the plurality of channel dividers is between about 2 mm and about 50 mm. In some embodiments, the height of the interior of the housing is between about 0.1 mm and about 5 mm. In some embodiments, the width of one or more of the plurality of channels is between about 0.1 mm and about 5 mm. In some embodiments, the plurality of channels is from about 2 to about 15 channels.

In some embodiments, the housing comprises a planer surface between the proximal end and distal end of the of the fluid collection device. In some embodiments, the housing comprises a curved surface between the proximal end and distal end of the of the fluid collection device. In some embodiments, a surface of the reservoir, plurality of channels, collection region, or a combination thereof comprises a hydrophobic material. In some cases, the hydrophobic material is coated on the surface by plasma treatment. In some cases, the hydrophobic material has a water contact angle greater than or equal to about 155°. In some embodiments, a surface of the reservoir, plurality of channels, liquid collection region, or a combination thereof comprises polytetrafluoroethylene (PTFE). In some embodiments, the housing comprises a plastic material. In some embodiments, the housing comprises a transparent material. In some embodiments, the casing comprises a thin layer of plastic material within the field of view of the plurality of sensors. In some cases, the thin layer has a thickness up to about 5 mm. In some cases, the plastic material comprises polyvinyl chloride, polycarbonate, polystyrene, polyester film, or a combination thereof. In some embodiments, the casing comprises one or more windows within the field of view of the plurality of sensors. In some cases, the one or more windows are transmissive to infrared at a wavenumber between about 3000 cm$^{-1}$ to about 4000 cm$^{-1}$. In some cases, the one or more windows have a thickness between about 0.1 mm and about 5 mm. In some cases, the one or more windows comprise polyvinyl chloride, polycarbonate, high density polyethylene, polystyrene, or a combination thereof.

In some embodiments, the sensing device further comprises a light source situated within the interior of the casing such that the slug is in the path of the light source. In some embodiments, the plurality of sensors is two sensors. In some embodiments, one or more of the plurality of sensors is an infrared sensor. In some embodiments, a sensor in the plurality of sensors is positioned between about 0.5 cm and about 10 cm from a second sensor in the plurality of sensors. In some embodiments, the method further comprises measuring a pressure of a wound environment by measuring a pressure at a first end of a pressure sensor conduit, wherein a first end of the pressure sensor conduit is positioned within the casing and a second end of the pressure sensor conduit is positioned at the wound environment. In some embodiments, the sensing device further comprises a controller configured to control the amount of negative pressure applied by the source of negative pressure. In some cases, the controller controls the amount of negative pressure applied by the source of negative pressure in response to a measurement of pressure. In some embodiments, the sensing device further comprises a display for displaying one or more parameters of the slug corresponding to measurements of the slug taken by the plurality of sensors. In some embodiments, the sensing device further comprising a power source. In some embodiments, the sensing device does not comprise a power source and power is supplied to the sensing device by an external unit connected to the sensing device.

DETAILED DESCRIPTION OF THE INVENTION

In one aspect of the disclosure, provided herein are devices and systems for collecting and sensing parameters of a fluid. In some embodiments, provided are fluid collection devices configured to collect liquid from a fluid comprising liquid and air, and then release the collected liquid as a column of liquid, which may be interchangeably referred to herein as a slug. The slug is then passed through a detection conduit where a sensor is positioned to detect a property of the slug, and thus the fluid input into the collection device. Systems for collecting and sensing parameters of a fluid may comprise a fluid collection device and the sensor for detecting the property of the slug formed during passage of fluid through the fluid collection device. For NPWT systems, the fluid collection device may be a disposable part of the system, while the sensor may be part of a durable or reusable portion of the system. As a non-limiting example, the sensor is part of a durable unit comprising a source of negative pressure drawing the fluid through the fluid collection device.

Figure 1:
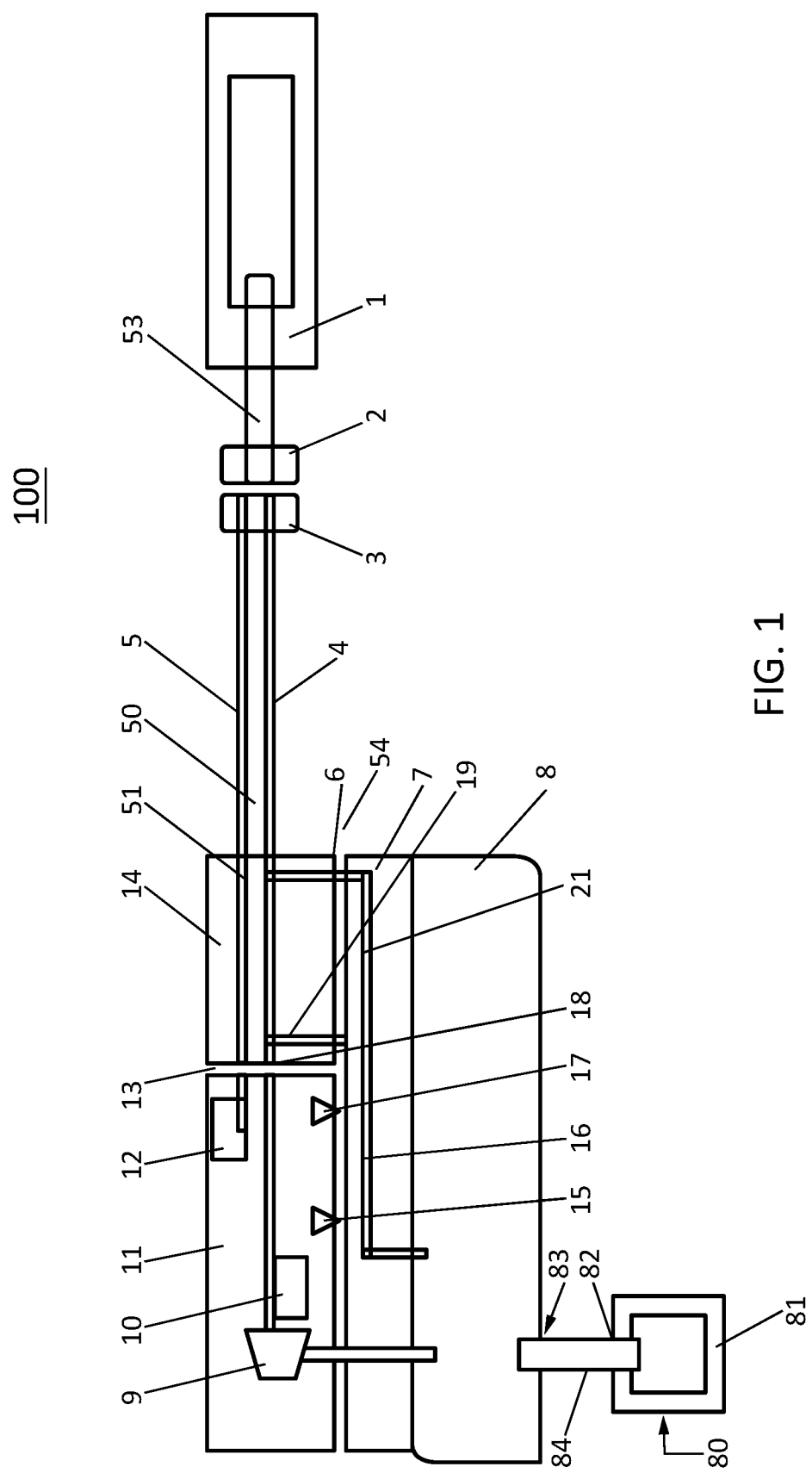
FIG. 1 shows an embodiment of a fluid flow sensing system for negative pressure wound therapy.

A system for sensing fluid flow comprising a fluid collection device and a flow sensor is shown in FIG. 1. System 100 is an NPWT system comprising a wound dressing 1 and a source of negative pressure, pump 9, for drawing fluid such as wound exudate from a space between wound dressing 1 and a wound into a canister 8. System 100 further comprises a connector 14 configured to provide communication between wound dressing 1, canister 8, and the main unit 11, which houses the pump 9.

Wound dressing 1 is connected to a wound dressing airway 53 comprising a first end in fluid communication with the underside of dressing 1, and a second end 2, the second end 2 configured to join with a first end 3 of tubing 4 and a sensing line 5. Both the tubing 4 and sensing line 5 are joined to connector 14 at attachment portion 50 of connector 14. Connector 14 comprises a sensing pathway 51 connecting sensing line 5 to a pressure sensor 12 via connection between an attachment portion 18 of connector 14 and an attachment portion 13 of a main unit 11, the main unit 11 comprising the pressure sensor 12. Connector 14 is connected to a fluid collection device 7 at an attachment portion 6 of connector 14 and an attachment portion 54 of the fluid collection device 7. The fluid collection device 7 comprises a fluid pathway 21 in fluid connection with detection conduit 16, which then opens to canister 8. Thus, the fluid pathway of system 100 is configured for fluid to be drawn from under dressing 1, through the dressing airway 53, through tube 4, through connector 14, through pathway 21, through detection conduit 16, and into canister 8.

The canister 8 comprises an outlet 83. A sensing device 80 includes a sensing device casing 81 having an inlet 82. The inlet 82 of the sensing device casing 81 is configured to be in fluid communication with the outlet 83 of the canister via a negative pressure conduit 84.

Negative pressure is communicated through system 100 to a site under dressing 1 from pump 9 housed within main unit 11. Negative pressure is applied from pump 9, through tube 19 of connector 14, through fluid collection device 7, through connector 14, through tubing 4, and through the dressing airway 53 to dressing 1.

Figure 2:
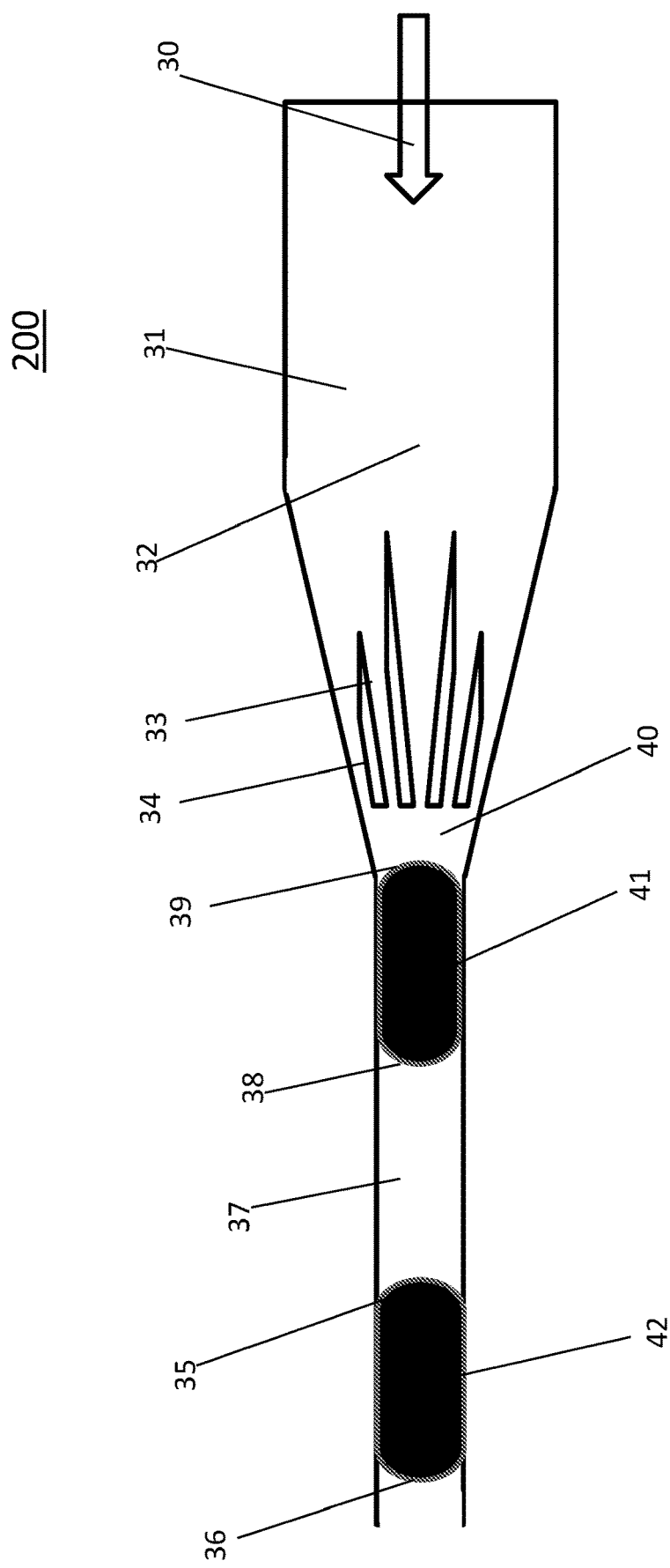
FIG. 2 shows a top view of a path for fluid flow through a first embodiment of a fluid collection device.
Figure 3:
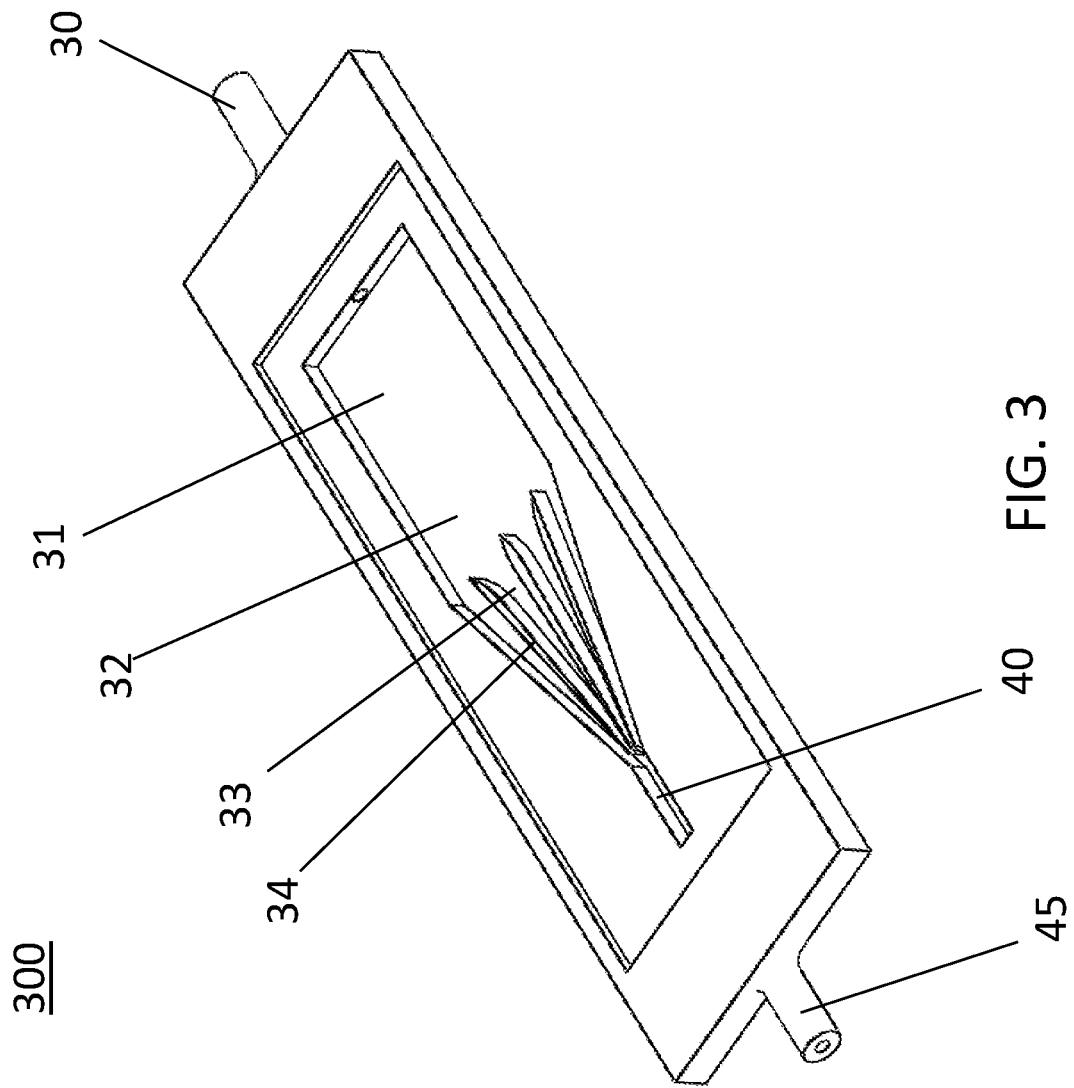
FIG. 3 shows an isometric representation of a second embodiment of a fluid collection device.

Fluid drawn through system 100 is separated into liquid slugs during passage of the fluid through fluid collection device 7. The slugs are released into detection conduit 16, which is positioned within the pathway of sensors 15 and 17, which are housed within main unit 11. Two embodiments of a fluid collection device 7 are shown in FIGS. 2-3.

An exemplary method for sensing fluid flow in system 100 comprises drawing exudate from a wound positioned under dressing 1 to canister 8 using the pressure difference between the dressing and the canister 8 connected to pump 9. Typically the exudate flow will be mixed with air, for example, due to small air leaks in the wound dressing. The pump is controlled by a controller that uses sensors 10 and 12 to sense the pressure in the canister 8 and sensing line 5, respectively. When exudate reaches the canister at 7, it is directed along the fluid pathway 21 of the fluid collection device 7 where it is partitioned into slugs of liquid, which are then passed through detection conduit 16. As a slug passes along detection conduit 16, it successively passes fluid detection sensors 17 and 15. These sensors may be the same or a different type of sensor and are inclusive of infrared optical sensors, capacitive sensors and thermal time of flight sensors. In the case of infrared sensors or transducers, the sensors detect the presence of water based liquids due to selective absorption. These sensors are available to one of skill in the art and include those that operate in reflective mode so both the light source and detector can be held in the main unit 11. The start and end of the slug is detected successively by sensors 17 and 15. By comparing the time delay between start and end of the slug passing the two sensors, both the speed and length of slug can be calculated. For system 100, the sensors are placed in the main unit 11 of the NPWT device such that they can sense the slug in the detection conduit 16 from their position within the main unit 11. In some embodiments, the main unit is a reusable portion of the system and the sensors are positioned such that they can sense through the main unit 11, for example, through thin layers of plastic or other suitable material that form the main unit 11 and/or detection conduit 16. In some embodiments, fluid conduit 16 is an open channel covered by a thin wall of an adhesive film. In some embodiments, the fluid conduit 16 is moulded into the top of canister 8.

The system of FIG. 1 is for illustrative purposes only and it is intended that a fluid sensing system may comprise additional components and/or lack one or more components shown. For example, one or more sensors within the main unit 11 may not be necessary for the system to function as described. As a further example, the connector 14 may be configured in a different manner or not present in the fluid sensing system.

The devices and systems described herein may be used with any canister available in the art, including the fluid collection apparatus described in the corresponding provisional application, filed on Jul. 8, 2017 as U.S. provisional patent application No. 62/360,211, concurrently with the provisional application to this application, the contents of which are fully incorporated herein.

Fluid Collection Device

In one aspect of the disclosure, provided herein are fluid collecting devices configured to collect liquid from a fluid input comprising a combination of liquid and air. The collected liquid may then be discharged from the device into a conduit as a column of liquid, or a slug, which can then be detected by one or more sensors. In some embodiments, a fluid collection device comprises: (a) a housing comprising an inlet and an outlet, the inlet located at a proximal end of the housing and the outlet located at a distal end of the housing; (b) a reservoir positioned within the housing at the proximal end of the housing; (c) a plurality of channel dividers positioned within the housing between the reservoir and the distal end of the housing, the plurality of channel dividers having a proximal end and a distal end; wherein the plurality of channel dividers define a plurality of fluid channels within the housing; (d) and a liquid collection region positioned within the housing between the distal end of the plurality of channel dividers and the distal end of the housing; wherein the housing comprises one or more fluid passageways connecting the inlet and the outlet through the interior of the housing; and wherein the reservoir, the plurality of channels, and the liquid collection region are in fluid communication within the one or more fluid passageways in the housing.

Fluid collection devices described herein are configured to accumulate liquid from a fluid, for example, within the plurality of flow channels, while air from the fluid bypasses the channels. Once all of the flow channels are filled with liquid, pressure from incoming air from the fluid pushes the liquid accumulated from the flow channels into the liquid collection region where the liquid is collected before being passed through a conduit as a slug. In some embodiments, the shape of a fluid collection device facilitates the accumulation and collection of liquid. In some embodiments, the width of the liquid collection region is smaller near the distal end of the housing than the width of the liquid collection region near the proximal end of the housing. In some cases, the fluid collection device is tapered and a proximal end of the reservoir has a width greater than the width of a distal end of the liquid collection region. As a non-limiting example, the width of the proximal end of the reservoir is about or at least about 2 to 5 times the width of the distal end of the liquid collection region. In some cases, the ratio of sizes can be as small as 1:1 provided there is a means of allowing air or gas to bypass liquid that is accumulating such that fluid and air are collated into discrete. The ratio of sizes can then be much larger while still providing the bypass function for air or gas. The limit of the size ratio is, at least in part, driven by the preferred size of liquid column for sensing and by the effect of the pressure difference needed to drive liquid through to the distal liquid region. If the ratio of volumes is large then the length of the liquid column becomes large and the pressure differential to drive the fluid consequently increases. The ratio of sizes relates to the ratio of lengths of liquid column entering and leaving the reservoir region. An alternative form to a planar reservoir includes a circular or conical form where the fluid channels are arranged around the circumference of the cone such that air or gas can bypass liquid that is accumulating in the fluid channels until the accumulated liquid bridges the last empty channel and the accumulated liquid is driven into the distal tubing as a column of liquid, or slug.

In some embodiments, the interior of the housing is configured to hold between about 100 uL and about 500 uL of fluid, or about 100 uL, 200 uL, 300 uL, 400 uL or 500 uL of fluid. In some cases, the interior of the housing holds about 200 uL of fluid. In some embodiments, the liquid collection region is configured to receive a slug of liquid having a volume between about 10 uL and about 200 uL, or about 10 ul, 20 ul, 50 ul, 80 ul, 100 ul, 120 ul, 150 ul, or 200 uL. In some cases, the liquid collection region is configured to receive a slug of liquid having a volume of about 100 uL. In some embodiments, a width of the liquid collection region is between about 0.5 mm and about 8 mm, or about 0.5 mm, 1 mm, 2 mm, 3 mm, 4 mm, 5 mm, 6 mm, 7 mm or 8 mm. In some cases, a first width of the liquid collection region is between about 0.5 mm and about 8 mm, and a second width of the liquid collection region is between about 0.5 mm and about 7 mm. In some embodiments, the length of the reservoir is between about 0.5 cm and about 5 cm, or between about 1 cm and about 2 cm. In some cases, the length of the reservoir is between about 1.5 cm and 2 cm. In some embodiments, the height of the reservoir is between about 0.1 mm and about 5 mm, or about 1 mm to 2 mm.

The configuration and length of the plurality of channel dividers facilitates accumulation of liquid within the channels defined by the channel dividers. A plurality of channel dividers includes about 2-15, 3-12, 3-10, 3-8 or 3-5 channel dividers. In some embodiments, the length of one or more of the plurality of channel dividers is between about 0.2 cm and about 5 cm, or about 0.2 cm, 0.5 cm, 1 cm, 1.5 cm, 2 cm, 2.5 cm, 3 cm, or 5 cm. In some embodiments, the height of one or more of the plurality of channel dividers is between about 0.1 mm and about 5 mm, or about 1 mm to about 2 mm. In many cases, the channel dividers extend from the bottom of the housing to the top of the housing such that when fluid is passed through the housing, if liquid is collected within the channels, air can only pass through an open channel. In such a configuration, once all open channels are filled with liquid, incoming air forces the collected liquid out of the channels to be released from the distal end of the housing as a column of liquid, or slug. In some embodiments, the width of one or more of the plurality of channels is between about 0.1 mm and about 5 mm, or between about 1 mm and about 3 mm. In some cases, the width is about 2 mm. In some cases, the plurality of channels have a reducing width from entrance to exit where the change in width is about 1 to 20 degrees, or typically about 5 degrees.

For fluid collection devices configured for use with a source of negative pressure, the device is configured to withstand pressures of up to about 200 mmHg without breaking. In general, for typically sized components of fluid collection devices described herein, a 0.5 mm to 1 mm thickness of plastic will provide adequate strength under pressures without breaking. For example, the forces due to the pressure differential, such as 200 mmHg applied over a square cm applies a load of about 2.6N. In some cases, the housing comprises a plastic material such as ABS (acrylonitrile-butadiene-styrene), PC (polycarbonate), PC-ABS, PP (polypropylene), HDPE (high-density polyethylene), or a combination thereof. In some cases, the housing comprises a transparent material.

The fluid collection device, or any region or surface thereof, may be substantially planar or flat, as well as have a curvature. The region or surface thereof includes any surface or portion of the housing, reservoir, channel divider, and liquid collection region. In some cases, a surface of a fluid collection device comprises one or more non-planar features, for example, a well and/or pillar. In some embodiments, housing comprises a planer surface from the proximal end to the distal end of the housing. In some embodiments, the housing comprises a curved surface from the proximal end to the distal end of the housing. An alternative form to a planar reservoir includes a circular conical form where the fluid channels are arrange around the circumference of the cone such that air or gas can bypass liquid that is accumulating in the fluid channels until the accumulated liquid bridges the last empty channel and the accumulated liquid is driven into the distal tubing. In some cases, this format is suited for use in line in fluid tubes where the overall circular cross section could be convenient.

In some embodiments, a surface of the reservoir, plurality of channels, liquid collection region, or a combination thereof comprises a hydrophobic surface. In some cases, the hydrophobic surface is applied using a plasma treatment available to one of skill in the art. This includes, but is not limited to, plasma treatments provided by Hennika Plasma. In some embodiments, a surface of the reservoir, plurality of channels, liquid collection region, or a combination thereof comprises a coating configured to enhance release of liquid from the surface. In some cases, a surface is coated with polytetrafluoroethylene. A non-limiting example of a surface coating that enhances liquid release is NANOMYTE® SuperCN, supplied by NEI Corporation.

In some embodiments, a fluid collection device comprises: (a) a housing comprising an inlet and an outlet, the inlet located at a proximal end of the housing and the outlet located at a distal end of the housing; (b) a reservoir positioned within the housing at the proximal end of the housing; (c) a plurality of channel dividers positioned within the housing between the reservoir and the distal end of the housing, the plurality of channel dividers having a proximal end and a distal end; wherein the plurality of channel dividers define a plurality of fluid channels within the housing; (d) and a liquid collection region positioned within the housing between the distal end of the plurality of channel dividers and the distal end of the housing; wherein the housing comprises one or more fluid passageways connecting the inlet and the outlet through the interior of the housing; and wherein the reservoir, the plurality of channels, and the liquid collection region are in fluid communication within the one or more fluid passageways in the housing. In some embodiments, the liquid collection region is configured to receive a slug of liquid having a volume between about 10 and about 200 uL. In some embodiments, the interior of the housing is configured to hold between about 100 uL and about 1000 uL of fluid and typically 500 uL. In some embodiments, the height of the reservoir, channels, liquid collection region, or any combination thereof, is between about 0.1 mm to about 5 mm, or typically about 1 mm to about 2 mm. In some embodiments, the reservoir has a width from about 5 mm to about 50 mm, or typically from about 15 mm to about 20 mm. In some embodiments, the reservoir has a length from about 5 mm to about 50 mm, or typically from about 15 mm to about 20 mm. In some embodiments, the proximal end of the housing has a width about 2 to 5 times the width of the distal end of the housing. In some embodiments, the proximal end of the liquid collection region has a width between about 0.5 mm and 8 mm, or typically about 5 mm. In some embodiments, the distal end of the liquid collection region has a width between about 0.5 mm and 7 mm, or typically about 3 mm. In some embodiments, the length of one or more of the plurality of channel dividers is between about 2 mm to 50 mm, or typically about 15 mm. In some embodiments, the width of one or more of the plurality of channels is between about 0.1 mm and about 5 mm, or typically about 2 mm. In some embodiments, the plurality of channels are tapered in the direction of flow by about 1 degree to 20 degrees, or typically about 5 degrees. In some embodiments, the plurality of channels is from about 2 to about 15 channels, or typically about 3 to 5 channels. In some embodiments, a surface of the reservoir, plurality of channels, liquid collection region, or a combination thereof comprises a hydrophobic material.

A top view of exemplary fluid passageways formed through an interior of a fluid collection device is shown in FIG. 2. Positioned at the proximal end of device 200 is reservoir 31, which receives fluid 30 through the inlet of the device (not shown). Positioned at the distal end of device 200 is a liquid collection region 40, which releases slugs of liquid 41 collected within region 40 to tube section 37. Positioned between reservoir 31 and liquid collection region 40 are four channel dividers 34, which define five channels 33. The plurality of channel dividers 34 has a tapered configuration, so that the proximal end of the plurality 32 is wider than the distal end of the plurality. This configuration facilitates accumulation of liquid within channels 33 near the distal end of the channels.

In an exemplary fluid collection method using device 200, fluid comprising a mixture of liquid and air enters the device at reservoir 31. The fluid is then drawn to channels 33 formed by channel dividers 34, where liquid from the fluid accumulates at the distal end of the channels due to the capillary force provided by the reducing section of the channels 33. Liquid accumulates in the channels 33 while continuing to allow air to pass through the remaining open channels. Periodically, all of the fluid channel 33 become blocked with liquid and as further air or fluid is drawn into the fluid collation device, this air or fluid drives the accumulated liquid forward to liquid collection region 40, where the liquid is then drawn along the tube section 37 as a slug of liquid 41. This cycle repeats such that air drawn into the device, for example, in NPWT from the dressing and/or any other system leaks, separated successive fluid slugs 41 and 42. By timing the start 36, 38 and end 35, 39 of the slugs, both the speed and length of the slugs can be determined. Knowledge of the cross sectional area of the tube section 37 then allows a volumetric flow to be calculated.

An isometric representation of an exemplary fluid collection device is shown in FIG. 3. Positioned at the proximal end of device 300 is reservoir 31, which receives fluid through the inlet 30 of the device housing. Positioned at the distal end of device 300 is a liquid collection region 40, which releases slugs of liquid collected within region 40 to outlet 45. Positioned between reservoir 31 and liquid collection region 40 are three channel dividers 34, which define four channels 33 having a proximal end 32 in communication with reservoir 31, and a distal end in communication with liquid collection region 40. In an exemplary method for fluid collection using device 300, fluid comprising liquid and air enters the device housing at inlet 30 and then collects in reservoir 31. As fluid is drawn from the reservoir 31 through the device, liquid from the fluid accumulates within channels 33, while air from the fluid bypasses the channels and passes through outlet 45. Liquid gradually fills channels 33 until there is no channel open for air to pass through. The accumulated liquid is forced to liquid collection region 40 as fluid continues to enter the housing. The liquid collected in region 40 is released from the device through outlet 45 and into a conduit for detection by one or more sensors as described elsewhere herein.

Flow Sensors

Liquid collected as a slug using a fluid collection device described herein may be detected by one or more flow sensors. In some embodiments, a flow sensor is housed within a durable or reusable portion of a system that can be used with more than one fluid collection device over time. As a non-limiting example, a flow sensor is housed in a main unit of a negative pressure system, the main unit comprising the source of negative pressure and optionally one or more additional elements, including pressure sensors. In some embodiments, a flow sensor is an infrared sensor known and available to one of skill in the art. As a non-limiting example a flow sensor is an infrared sensor such as a reflective optical sensor. Particular examples of reflective optical sensors include those made by Broadcom, part number HSDL-9100-024. Such sensors combine an analogue-output reflective sensor with an IR emitter and photodiode. These sensors have a typical rise time of 50 ns and typical fall time of 50 ns, which minimizes timing delays to detecting the start and end of liquid slugs. Further sensors available to those of skill in the art include tube sensors, such as those produced by Optek Technology, part number OPB350. Such tube sensors operate for tubing of a specific size, for example, ⅛th inch tubing, and operate such that clear liquid present causes the phototransistor to sink the maximum current, while dark liquid present causes it to sink the minimum current. These sensors may have a slower response time, less than 50 microseconds rise time and a fall time in the region of 50 to 250 microseconds, however, still provide a response time suitable for use in the methods described herein.

In one aspect, provided herein is a sensing device for use with a fluid collection device as described elsewhere herein. In some embodiments, the sensing device is part of a main unit of a negative pressure system, wherein the main unit comprises both a source of negative pressure and one or more flow sensors for detecting liquid collected as a slug using a fluid collection device. In some embodiments, a sensing device comprises a casing comprising a source of negative pressure and one or more flow sensors situated within the casing such that a material located outside of the casing is in the field of view of the sensors. A non-limiting example of a flow sensor is an infrared sensor. In some cases, the sensing device comprises a plurality of flow sensors, the plurality comprising about 2, 3, 4, 5, 6, 7, 8, 9 or 10 flow sensors. For some instances where the sensing device comprises two or more flow sensors, a first flow sensor is positioned between about 0.5 cm and about 4 cm, or typically about 2 cm from a second flow sensor, as measured center-to-center.

In some embodiments, the casing comprises a thin layer of plastic within the field of view of the flow sensor. Plastics include, polyvinyl chloride, polycarbonate, high density polyethylene, polystyrene, and any other plastic having suitable infrared transmittance at the frequency where liquid is absorbing. In some embodiments, a casing has a typical thicknesses from about 0.1 mm as a film to about 3 mm as a moulding. In some embodiments, a film bonded over an open channel is used. In some embodiments, a casing comprises a moulded section of about 1 mm to about 1.5 mm thickness. In some embodiments, the casing comprises one or more windows within the field of view of the flow sensor which can allow the main casework to be of an infrared absorbing material and to still provide visibility of the fluid for the sensors. The windows can be provided by plastics that are transmissive of infrared at wave-numbers between 3000 and 4000 cm$^{-1}$. In some cases, a thickness of the window is between about 0.1 mm and about 5 mm, or about 1 to 1.5 mm. In some embodiments, the window is comprised of a plastic, for example, polyvinyl chloride, polycarbonate, high density polyethylene, polystyrene, or a combination thereof. Alternatively, the window is an open window with a transmissive-reflective sensor as known to one of skill in the art. By way of example, a Broadcom sensor, part number HSDL-9100-024. The transmissive-reflective sensor is positioned either close to the window or fitted into the aperture within the casework. In some embodiments, the sensing device further comprises a light source situated within the interior of the casing such that the material located outside of the casing is in the path of the light source. In many implementations, a sensor and light source are combined as a unit as described above.

In some embodiments, the flow sensor is housed with one or more pressure sensors. Pressure sensors suitable are known to those of skill in the art. Non-limiting examples of pressure sensors include: Omron part number SMPP03, range +/−50 kPa; Honeywell, part number ABP L LN N 250 MD A A 3, range +/−250 mbar; and NXP, part number MPXV7025DP, with range −25 kPa to 25 kPa. Fluid sensors then include those as described, such as reflective optical sensors made by Broadcom, part number HSDL-9100-024 and Optek Technology, part number OPB350.

As a non-limiting example, one of the one or more pressure sensors is configured to detect a pressure of a wound environment by measuring a pressure at a first end of a conduit positioned within the casing, wherein the second end of the conduit is positioned at the wound environment. As another example, one of the one or more pressure sensors is configured to detect a pressure of a canister by measuring a pressure at a first end of a conduit positioned within the casing, wherein the second end of the conduit is positioned within the canister; and wherein the conduit is configured to apply a negative pressure from the source of negative pressure to the canister.

In some embodiments, the sensing device comprises a controller configured to control an amount of negative pressure applied by the source of negative pressure. In some embodiments, the source of negative pressure comprises a diaphragm pump. Diaphragm pumps are available to one of skill in the art and include, by way of example, those provided by Gardener Denver, model number 2002, 3003 or 3013; KNF part numbers NMS010S or NMS020S; and Koge, part number KPV08A-3A or KPV14A. In some implementations where the sensing device comprises a pressure sensor, the controller controls the amount of negative pressure applied by the source of negative pressure in response to a measurement of pressure by one or more pressure sensors. In some embodiments, a sensing device comprises a display for displaying one or more parameters of the material corresponding to measurements of the material taken by the plurality of infrared sensors. In some embodiments, a sensing device comprises a power source for providing power to the source of negative pressure, controller, display, or a combination thereof. In some embodiments, a sensing device lacks a power source for powering the source of negative pressure, controller, display, or a combination thereof, and the power source is provided by an external unit connected to the sensing device. As a non-limiting example, a connector, such as connector 14 exemplified in FIG. 1, provides the power source. A source of power includes a battery, such as an alkaline or lithium ion battery, for example, a CR123A cell as provided by manufactures such as Panasonic or Duracell or AA lithium batteries such as those supplied by Energiser. In some other cases, a rechargeable battery is used, such as a lithium polymer cell as supplied by Panasonic or Sanyo of NIMH batteries supplied by companies such as Panasonic and FDK.

A non-limiting example of a sensing device is shown as the main unit 11 in the system 100 of FIG. 1. Main unit 11 comprises two flow sensors 15 and 17, such as infrared sensors, a pump 9, and pressure sensors 10 and 12. Flow sensors 15 and 17 are positioned adjacent a side of the unit 11 configured to allow for a material located outside of the casing to be in the field of view of, and detected by, the sensors.

Systems and Methods

In one aspect of the disclosure, provided herein are systems comprising a fluid collection device and/or flow sensing device as described herein. In some embodiments, provided is a device system comprising the fluid collection device and flow sensing device. Systems provided herein may further comprise one or more accessory elements, for example, elements useful for performing a negative pressure therapy. In some embodiments, an accessory comprises a wound dressing. In some embodiments, an accessory comprises a collection canister. In some embodiments, an accessory comprises one or more conduits or tubings configured to connect to the dressing, canister, and/or sensing device. In some embodiments, an accessory comprises a connector configured to connect the dressing to a collection canister, connect the collection canister to the sensing device, and connect the dressing to the sensing device.

In some embodiments, provided herein is a system comprising a fluid collection device and a fluid collection canister. The fluid collection device may be an integral component of the collection device, or operably connected to the collection device via one or more connectors and/or tubings. The fluid collection device can be formed as a combination of an open channel moulded into the top of the canister and sealed by a film. Alternatively the fluid collection device is built into the connector that connects the dressing to the main unit and the fluid channel can be made from two or more moulded components bonded or sealed together by adhesive, sealant or welding. Similarly, the fluid channel can be formed by a thin film bonded to cover and seal an open channel. The outward (distal) end of the fluid collection device is then connected to the canister via a sealed connection provided by means such as an O ring seal or face seal.

In some embodiments, provided herein is a fluid flow sensing system comprising a fluid collection device, a canister, and a sensing device. The fluid collection device of the fluid flow sensing system comprises a housing having an inlet located at a proximal end of the fluid collection device and an outlet located at a distal end of the fluid collection device, the interior of the housing comprising: a reservoir, a plurality of channel dividers defining a plurality of fluid channels, and a liquid collection region; wherein the housing comprises one or more fluid passageways connecting the inlet and the outlet through the interior of the housing; and wherein the reservoir, the plurality of channels, and the liquid collection region are in fluid communication within the one or more fluid passageways in the housing. The canister of the fluid flow sensing system comprises an inlet and an outlet, the inlet of the canister in fluid communication with the outlet of the fluid collection device housing via a detection conduit. In some fluid flow sensing systems, the fluid collection device is integral with the canister. The sensing device of the fluid flow sensing system comprises a casing having an inlet, a source of negative pressure and a plurality of sensors; the inlet of the sensing device casing in fluid communication with the outlet of the canister via a negative pressure conduit. In some fluid flow sensing systems, the source of negative pressure comprises a diaphragm pump. In some cases, the plurality of sensors comprises from about 2 to about 5 flow sensors. An exemplary flow sensor is an infrared sensor. In some cases, the plurality of flow sensors comprises two infrared sensors.

In some embodiments, the fluid flow sensing system further comprises a connector. The connector may house at least a portion of the negative pressure conduit. In some cases, the connector comprises a power source for providing power to the source of negative pressure.

In some embodiments, the detection conduit comprises plastic material, such as polyvinyl chloride, polycarbonate, high density polyethylene, polystyrene, or a combination thereof. In some embodiments, the conduit has a thickness of about 0.1 mm to about 3 mm, or typically about 0.1 mm thick if a film of plastic is used and about 0.5 mm to 1.5 mm thick if a moulded wall is used. In some embodiments, the detection conduit has an inner diameter of less than or equal to about 5 mm, or typically about 1 to 3 mm. In some embodiments, the volume of the slug to be detected is between about 10 uL and about 3000 uL, or typically about 30 uL. In some embodiments, the length of the slug to be detected is between about 1 mm and about 100 mm, or typically between about 20 mm and 80 mm.

In some embodiments, the sensing device further comprises a pressure sensor. For some methods employing the fluid flow sensing system, application of negative pressure from the source of negative pressure is modulated to maintain a predetermined pressure within the negative pressure conduit.

The fluid collection device of the flow sensing system may be configured and sized as appropriate to enable the collection of liquid from a fluid mixture of liquid and air. As a non-limiting example, the fluid collection device comprises from about 3 to about 8 channel dividers defining from about 4 to about 9 channels for accumulating fluid prior to fluid collection and release as a slug of liquid. In some embodiments, the plurality of fluid channels is configured to accumulate between about 20 uL and about 300 uL of liquid. In some cases, the length of one or more of the plurality of channel dividers is between about 0.5 cm and about 2 cm. In some embodiments, the height of one or more of the plurality of channel dividers is between about 0.5 mm and about 2 mm. In some embodiments, the width of one or more of the plurality of channels is between about 0.5 mm and about 2 mm. In some embodiments, the fluid collection device is tapered and a proximal end of the reservoir has a width greater than the width of a distal end of the liquid collection region. In some embodiments, the width of the proximal end of the reservoir is at least about 5× the width of the distal end of the liquid collection region. As a non-limiting example, the width of the liquid collection region is between about 5 mm and about 20 mm. In some cases, the length of the reservoir is between about 0.5 cm and about 3 cm. In some embodiments, the height of the reservoir is between about 1 mm and about 2 mm. In some embodiments, the housing comprises a plastic material.

In some embodiments, the casing of the sensing device comprises a thin layer of plastic material so that a flow sensor positioned next to the thin layer of plastic material detects a slug located on the other side of the thin layer of plastic material. In general, depending on the particular sensor selected, the distance between the sensor and fluid conduit should be sized to match the sensor. Some sensors are set for detection distances of a few millimeters (1 to 5 mm) and others are set for longer ranges not limited to 50 mm. In some embodiments, the sensing device further comprises a light source situated within the interior of the casing such that the slug is in the path of the light source. In some embodiments, the sensing device further comprises a controller configured to control the amount of negative pressure applied by the source of negative pressure. As a non-limiting example, the controller controls the amount of negative pressure applied by the source of negative pressure in response to a measurement of pressure. In some embodiments, the sensing device further comprises a display for displaying one or more parameters of the slug corresponding to measurements of the slug taken by the plurality of sensors. In some embodiments, the sensing device further comprises a power source. In further embodiments, the sensing device does not comprise a power source and power is supplied to the sensing device by an external unit connected to the sensing device.

A non-limiting method for sensing fluid using a fluid flow sensing system comprises applying a negative pressure from the source of negative pressure to the fluid collection device via the canister to draw a fluid mixture of liquid and air through the inlet of the fluid collection device and along the one or more fluid passageways of the fluid collection device housing; wherein the liquid of the fluid mixture accumulates at the plurality of flow channels while the air of the fluid mixture passes through flow channels until the plurality of flow channels have accumulated liquid of the fluid mixture; drawing the accumulated fluid into the liquid collection region as a slug of liquid when the plurality of flow channels become blocked with the accumulated fluid; drawing the slug from the liquid collection region, through the outlet of the fluid collection housing, and through the detection conduit; and detecting passage of the slug through the detection conduit with the plurality of sensors. In some embodiments, the fluid provided to the fluid collection apparatus comprises less than or greater than about 5% of air by volume. In other embodiments the fluid provided to the fluid collection apparatus comprises less than or greater than about 1% of liquid by volume. For applications of NPWT, the ratio of the percentage of air to liquid depending on the ratio of exudates flow from the patient and the rate of air leak into the dressing. Suitable negative pressures applied in such a method include pressures between about 80 and about 125 mmHg below atmospheric pressure.

In some embodiments, the time it takes for the beginning of the slug to reach each of the plurality of sensors is detected successively; and the time it takes for the end of the slug to reach each of the plurality of sensors is detected successively. Some methods comprise comparing the time delay between the beginning and the end of the liquid slug passing the plurality of sensors to calculate the speed and length of the slug. The rate of the flow of the mixture from the fluid collection device can also then be calculated.

The method for sensing fluid flow may be performed as part of a negative pressure wound therapy, where the fluid drawn to the canister is exudate from the wound of a patient and the inlet of fluid collection device is fluidically connected to the wound site of the patient via a wound conduit. In some methods, the canister is positioned relative to the patient in an orientation-independent manner.

EXAMPLES

Example 1

Fluid Collection Device

A fluid collection device as generally shown by 2 was manufactured. Positioned at the proximal end of the device is a reservoir having a 15-20 mm width and 15-30 mm length, and configured to receive through an inlet of the device. Positioned at the distal end of the device is a liquid collection region having a 1-10 mm length, 0.5-8 mm proximal width, 0.5-7 mm distal width, and configured to releases slugs of liquid collected within this region to a tube. Positioned between the reservoir and liquid collection region are four channel dividers defining five channels. Each flow divider is 0.1-5 mm in width, defining channels having 0.1-5 mm widths. The dividers are tapered to 1-20 degrees, so that the proximal end of the plurality is wider than the distal end of the plurality. This configuration facilitates accumulation of liquid within the channels near the distal end of the channels. The overall length of the device is 75 mm, with a 30 mm width.

Example 2

Flow Sensing

The fluid collection device of Example 1 was used to collect slugs of liquid from a fluid input comprising a mixture of fluid and air. The nominal flow of liquid was set to 3 cc per minute and an air flow of 10 cc per minute was mixed with the liquid so that a two phase flow was established. When the slugs were collated by the device of Example 1, they were passed through a detection conduit where they were detected by a pair of infrared sensors. The infrared sensors were of the type made by Optek Technology, part number OPB350 and the pair of sensors were placed 50 mm apart.

Figure 4:
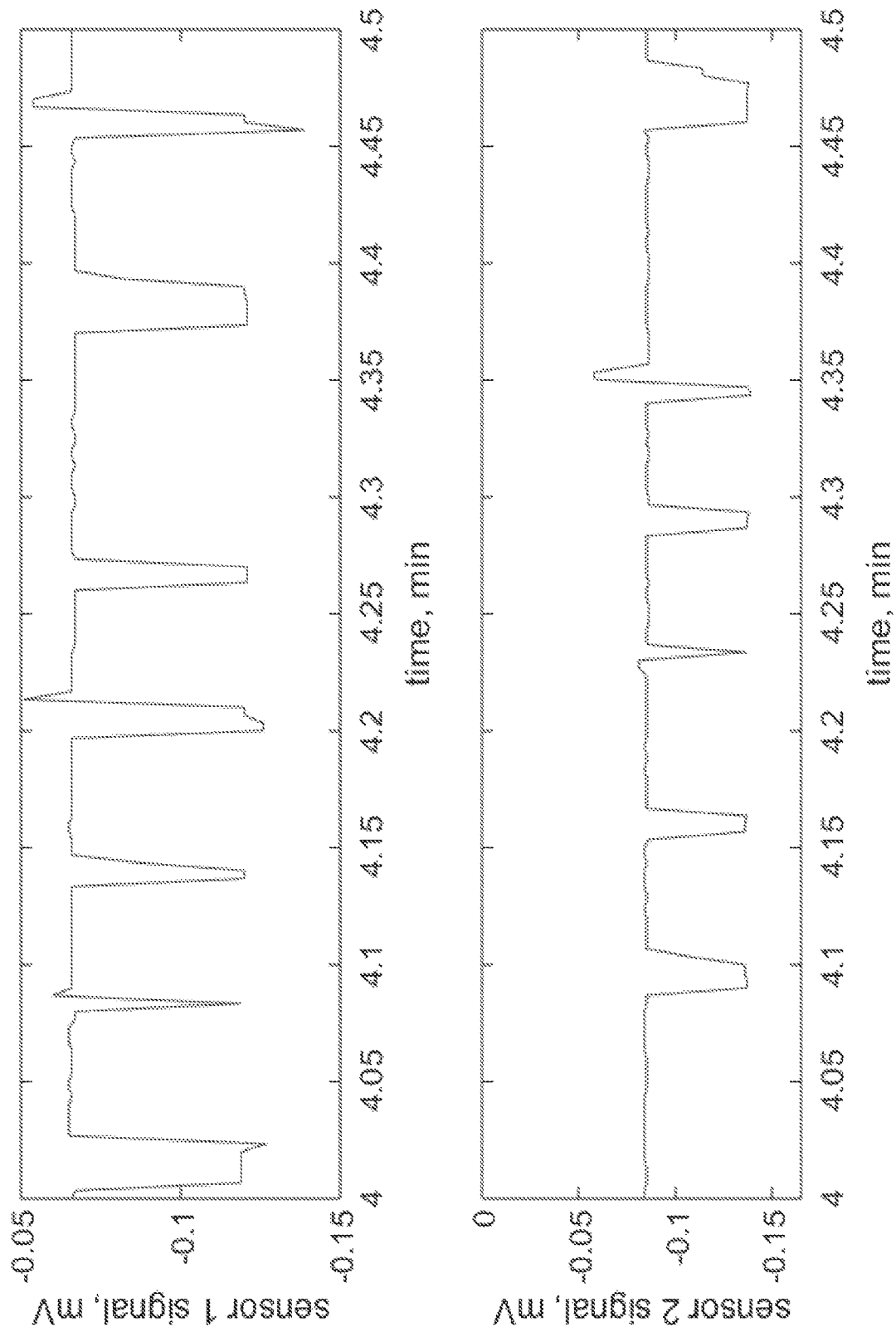
FIG. 4 shows graphs of response signals from two sensors in a sensing device detecting the passage of slugs through a detection conduit for 1 min.
Figure 5:
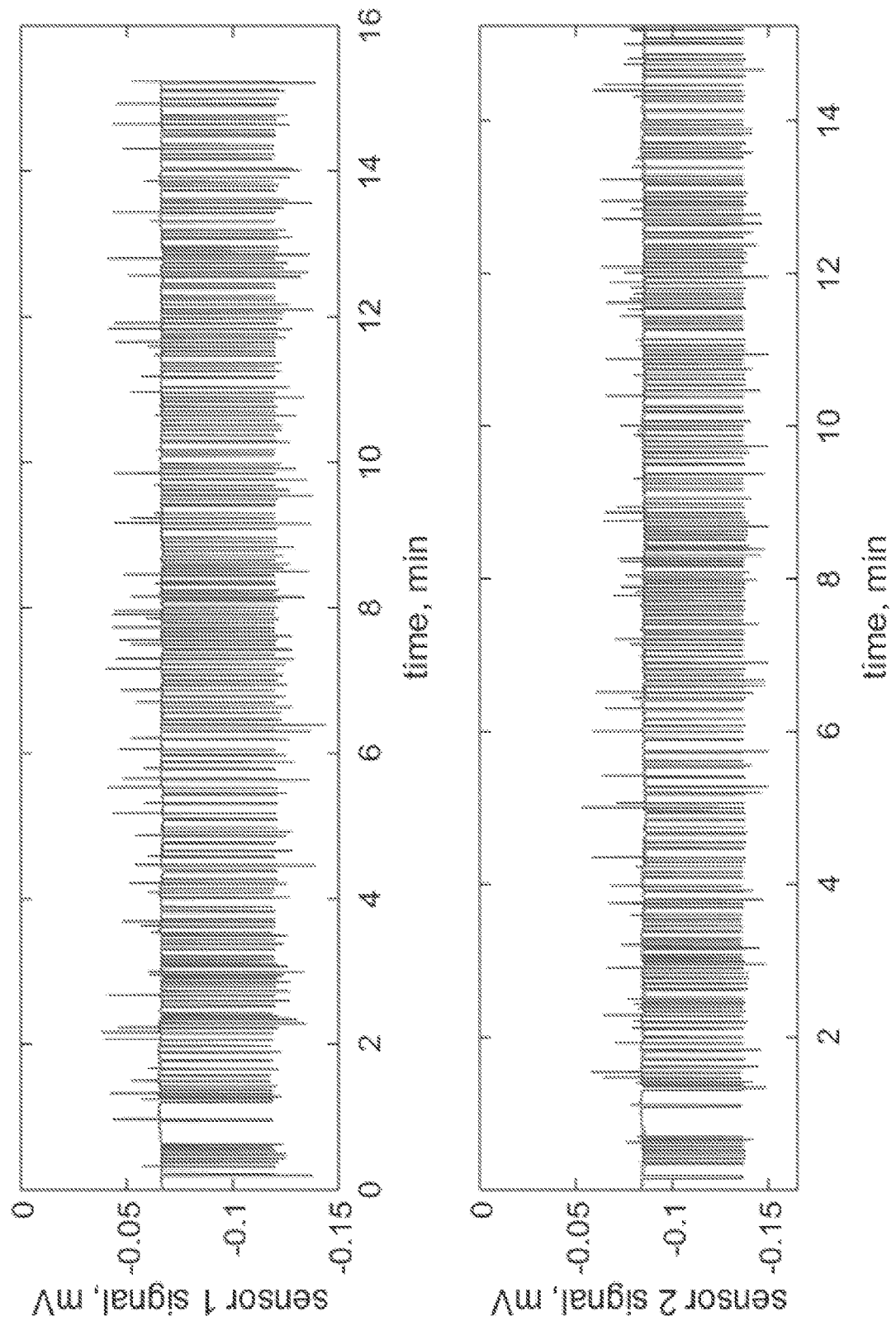
FIG. 5 shows graphs of response signals from two sensors in a sensing device detecting the passage of slugs through a detection conduit for 15 min.
Figure 6:
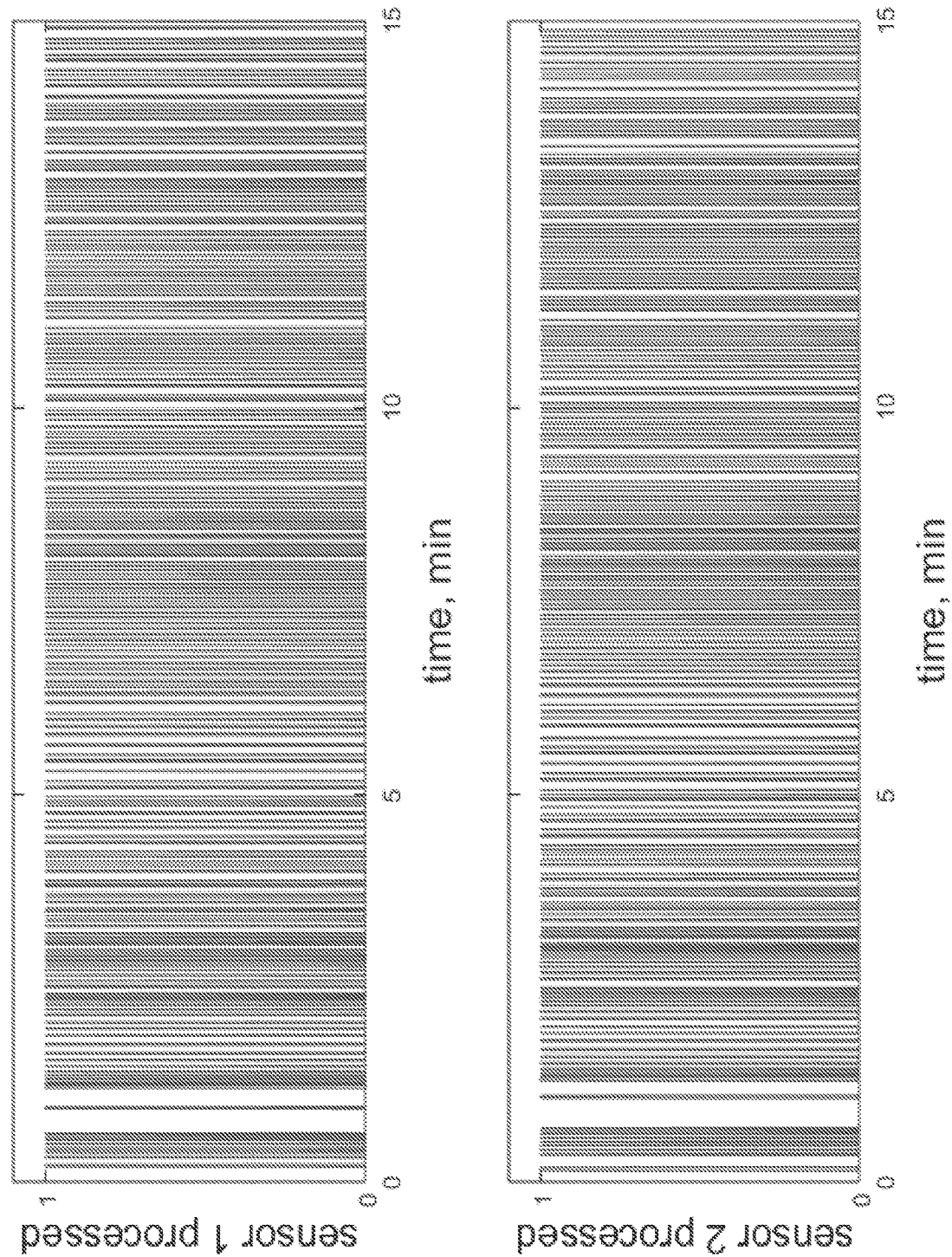
FIG. 6 shows graphs of processed response signals from the graphs of FIG. 5.
Figure 7:
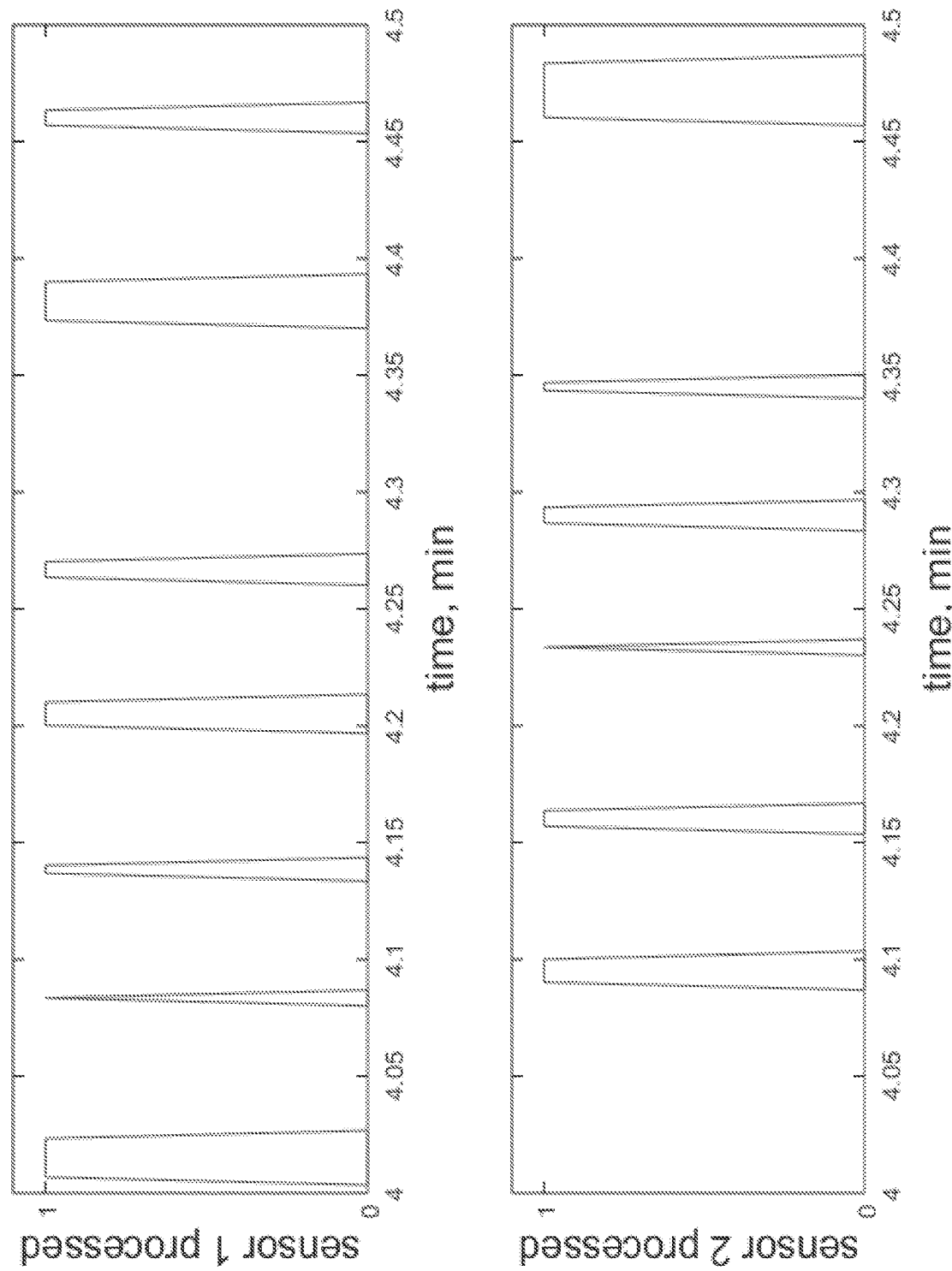
FIG. 7 shows a section of the processed response signal from the graphs of FIG. 6, indicating when flow is detected.
Figure 8:
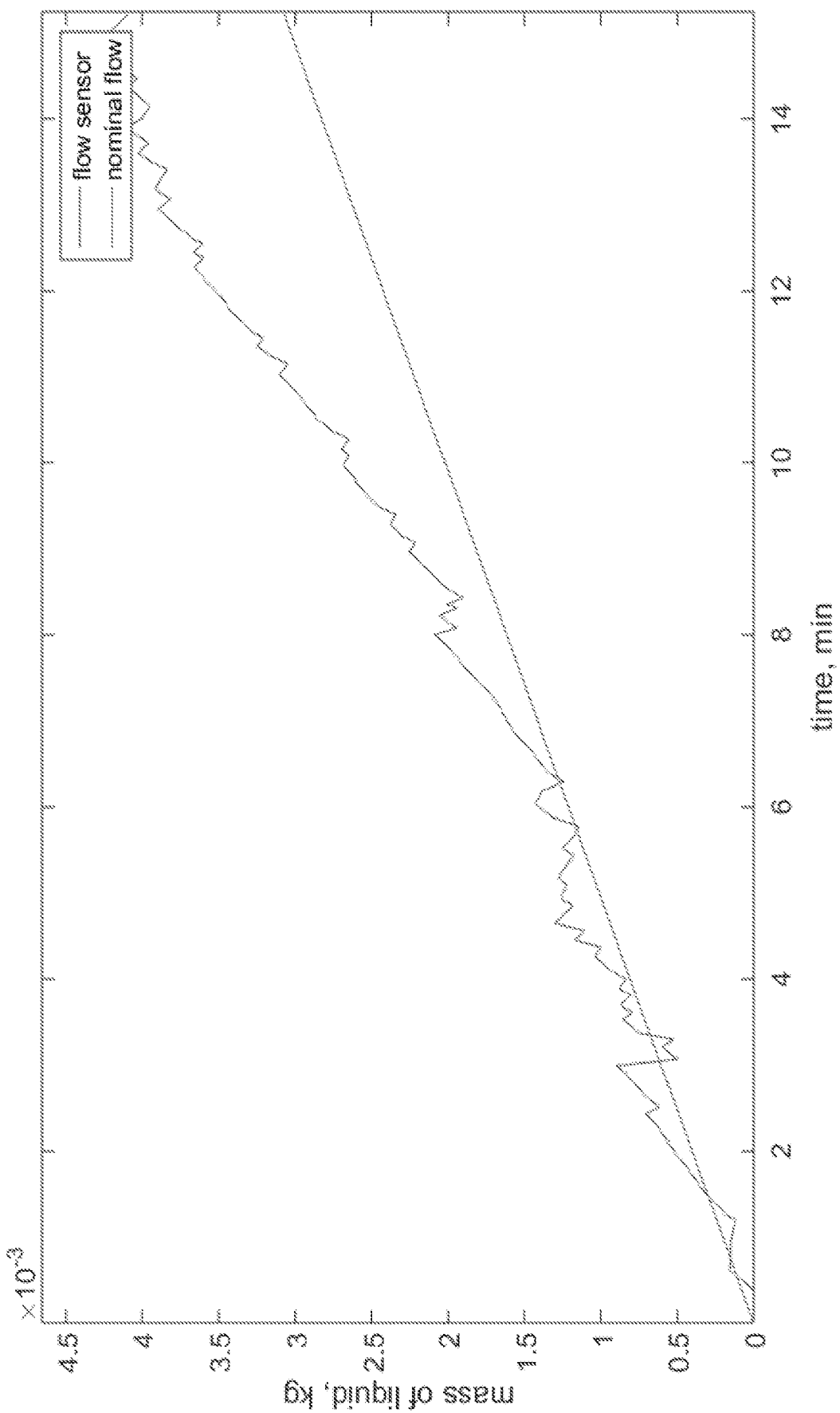
FIG. 8 shows graphs plotting the mass of liquid detected flowing through the detection conduit as a function of time in minutes, and the nominal mass of liquid actually flowing through the detection conduit as a function of time in minutes.

FIG. 4 shows graphs of response signals from the two sensors as the slugs passed through the detection conduit for 1 min. FIG. 5 shows graphs of response signals from the two sensors as the slugs passed through the detection conduit for 15 min. FIG. 6 shows graphs of processed response signals from the graphs of FIG. 5. FIG. 7 shows a section of the processed response signal from the graphs of FIG. 6, indicating when flow was detected. FIG. 8 shows graphs plotting the mass of liquid detected flowing through the detection conduit as a function of time in minutes, and the nominal mass of liquid actually flowing through the detection conduit as a function of time in minutes.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. A fluid collection device comprising:
   a) a housing comprising an inlet and an outlet, the inlet located at a proximal end of the housing and the outlet located at a distal end of the housing;
   b) a reservoir positioned within the housing at the proximal end of the housing;
   c) a plurality of channel dividers positioned within the housing between the reservoir and the distal end of the housing, the plurality of channel dividers having a proximal end and a distal end; wherein the plurality of channel dividers define a plurality of fluid channels within the housing; and
   d) a liquid collection region positioned within the housing between the distal end of the plurality of channel dividers and the distal end of the housing;
   wherein the housing comprises one or more fluid passageways connecting the inlet and the outlet through the interior of the housing; and wherein the reservoir, the plurality of channels, and the liquid collection region are in fluid communication within the one or more fluid passageways in the housing; and
   wherein the fluid collection device is configured to collect liquid from a fluid comprising liquid and air, and then release the collected liquid as a slug.

2. The fluid collection device of claim 1, wherein the fluid collection device is tapered and a proximal end of the reservoir has a width greater than the width of a distal end of the liquid collection region.

3. The fluid collection device of claim 1, wherein the liquid collection region is configured to receive a slug of liquid having a volume between about 10 uL and about 200 uL.

4. The fluid collection device of claim 1, wherein the length of one or more of the plurality of channel dividers is between about 2 mm and about 50 mm.

5. The fluid collection device of claim 1, wherein the width of one or more of the plurality of channels is between about 0.1 mm and about 5 mm.

6. The fluid collection device of claim 1, wherein the width of one or more of the plurality of channels is tapered to reduce direction of flow by about 1 degree to about 20 degrees.

7. The fluid collection device of claim 1, wherein a surface of the reservoir, plurality of channels, liquid collection region, or a combination thereof comprises a hydrophobic material.

8. The fluid collection device of claim 7, wherein the hydrophobic material has a water contact angle greater than or equal to about 155°.

9. The fluid collection device of claim 1, wherein a surface of the reservoir, plurality of channels, liquid collection region, or a combination thereof comprises polytetrafluoroethylene (PTFE).

10. The fluid collection device of claim 1, wherein the housing comprises a transparent material.

11. A canister comprising or operably connected to the fluid collection device of claim 1.

12. A fluid collection system comprising the fluid collection device of claim 1 and a canister, wherein the outlet of the fluid collection device is in fluid communication with an inlet of the canister.

13. A fluid collection system comprising the fluid collection device of claim 1 and a wound dressing, wherein the inlet of the fluid collection device is in fluid communication with an outlet of the wound dressing.

14. A fluid collection system comprising the fluid collection device of claim 1 and a sensing device comprising:
   a plurality of infrared sensors situated within a casing such that a column of liquid located outside of the casing is in the field of view of the plurality of infrared sensors.

15. A fluid flow sensing system comprising:
   a) a fluid collection device comprising a housing having an inlet located at a proximal end of the fluid collection device and an outlet located at a distal end of the fluid collection device, the interior of the housing comprising: a reservoir, a plurality of channel dividers defining a plurality of fluid channels, and a liquid collection region; wherein the housing comprises one or more fluid passageways connecting the inlet and the outlet through the interior of the housing; and wherein the reservoir, the plurality of channels, and the liquid collection region are in fluid communication within the one or more fluid passageways in the housing;
   b) a canister comprising an inlet and an outlet, the inlet of the canister configured to be in fluid communication with the outlet of the fluid collection device housing via a detection conduit; and
   c) a sensing device comprising: a casing having an inlet, a source of negative pressure and a plurality of sensors; the inlet of the sensing device casing configured to be in fluid communication with the outlet of the canister via a negative pressure conduit.

16. The fluid flow sensing system of claim 15, wherein the inlet of fluid collection device is configured to be connected to a wound site of a patient via a wound conduit.

17. The fluid flow sensing system of claim 15, wherein the detection conduit has an inner diameter of less than or equal to about 0.5 mm to about 5 mm.

18. The fluid flow sensing system of claim 15, wherein the source of negative pressure comprises a diaphragm pump.

19. The fluid flow sensing system of claim 17, wherein the detection conduit comprises a material transmissive of infrared at a wavenumber between about 3000 cm·1 to about 4000 cm·1.

20. The fluid flow sensing system of claim 15, further comprising a pressure sensor.

21. A method for sensing fluid flow, the method comprising:
   a) providing:
      i) a fluid collection device comprising a housing having an inlet located at a proximal end of the fluid collection device and an outlet located at a distal end of the fluid collection device, the interior of the housing comprising: a reservoir, a plurality of channel dividers defining a plurality of fluid channels, and a liquid collection region; wherein the housing comprises one or more fluid passageways connecting the inlet and the outlet through the interior of the housing; and wherein the reservoir, the plurality of channels, and the liquid collection region are in fluid communication within the one or more fluid passageways in the housing;
      ii) a canister comprising an inlet and an outlet, the inlet of the canister in fluid communication with the outlet of the fluid collection device housing via a detection conduit; and
      iii) a sensing device comprising: a casing having an inlet, a source of negative pressure and a plurality of sensors; the inlet of the sensing device casing in fluid communication with the outlet of the canister via a negative pressure conduit;
   b) applying a negative pressure from the source of negative pressure to the fluid collection device via the canister to draw a fluid mixture of liquid and air through the inlet of the fluid collection device and along the one or more fluid passageways of the fluid collection device housing; wherein the liquid of the fluid mixture accumulates at the plurality of flow channels while the air of the fluid mixture passes through flow channels until the plurality of flow channels have accumulated liquid of the fluid mixture;
   c) drawing the accumulated fluid into the liquid collection region as a slug of liquid when the plurality of flow channels become blocked with the accumulated fluid;
   d) drawing the slug from the liquid collection region, through the outlet of the fluid collection housing, and through the detection conduit; and
   e) detecting passage of the slug through the detection conduit with the plurality of sensors.

22. The method of claim 21, wherein the time it takes for the beginning of the slug to reach each of the plurality of sensors is detected successively; and wherein the time it takes for the end of the slug to reach each of the plurality of sensors is detected successively.

23. The method of claim 22, further comprising comparing the time delay between the beginning and the end of the liquid slug passing the plurality of sensors to calculate the speed and length of the slug.

24. The method of claim 23, further comprising calculating the rate of the flow of the mixture from the fluid collection device.

25. The method of any claim 21, wherein the inlet of fluid collection device is connected to a wound site of a patient via a wound conduit, and the fluid mixture drawn through the inlet of the fluid collection device is fluid drawn from the wound site of the patient.

26. The method of claim 25, wherein the fluid collection device is connected to the wound site of the patient in an orientation-independent manner.

* * * * *